United States Patent
De Bokx

[11] Patent Number: 5,684,857
[45] Date of Patent: Nov. 4, 1997

[54] METHOD FOR GE-XRF X-RAY ANALYSIS OF MATERIALS, AND APPARATUS FOR CARRYING OUT THE METHOD

[75] Inventor: Pieter K. De Bokx, Eindhoven, Netherlands

[73] Assignee: U.S. Philips Corporation, New York, N.Y.

[21] Appl. No.: 591,132

[22] Filed: Jan. 25, 1996

[30] Foreign Application Priority Data

Jan. 27, 1995 [EP] European Pat. Off. ............. 95200199

[51] Int. Cl.$^6$ .............................................. G01N 23/223
[52] U.S. Cl. .............................................. 378/45; 378/44
[58] Field of Search ........................... 378/44, 45, 49, 378/70, 73, 76, 79, 83, 84

[56] References Cited

U.S. PATENT DOCUMENTS

| | | | |
|---|---|---|---|
| 5,192,869 | 3/1993 | Kumakhov | 250/505.1 |
| 5,305,366 | 4/1994 | Nakahara et al. | 378/45 |
| 5,537,451 | 7/1996 | Serebryakow et al. | 378/45 |

FOREIGN PATENT DOCUMENTS

| | | | |
|---|---|---|---|
| 363262 | 7/1981 | Austria | G01N 23/22 |

OTHER PUBLICATIONS

T. Noma et al, "Surface analysis of layered thin films using a synchrotron x-ray microbeam combined with a grazing-exit condition", Rev. Sci Instrum. 65 (4), Apr. 1994, pp. 837–844.

J.R. Rhodes, "Advances In X-Ray Analysis", vol. 23, Plenum Press, New York and London, pp. 263–272. no date.

E.P. Bertin, "Principles and Practice of X-ray Spectrometric Analysis" 2nd ed., Plenum Press, New York–London, chapter 6, paragraph 4, pp. 247–257. no date.

A.M. Cormack, "Inverse Problems", American Mathematical Society, Providence Rhode Island, Apr. 12–13, 1983, SIAM–AMS Proceedings, vol. 14, pp. 33–39.

Primary Examiner—Don Wong
Attorney, Agent, or Firm—Anne E. Barschall

[57] ABSTRACT

A method for GE-XRF (Grazing Exit X-Ray Fluorescence) with high spatial resolution in the direction parallel as well as perpendicular to the specimen surface. The specimen (2) to be examined is irradiated by means of an X-ray beam having a cross-section which is substantially larger than the surface region to be examined. This beam irradiates a large number of parts of the specimen surface and the respective radiation thus excited is measured each time. From all measurements the intensity of the radiation excited by individual pixels in the specimen is calculated by means of a suitable algorithm. The advantage of this method resides in the fact that an X-ray source having a very high intensity (for example, a synchrotron) can be dispensed with and suitable spatial resolution is achieved nevertheless.

8 Claims, 2 Drawing Sheets

METHOD FOR GE-XRF X-RAY ANALYSIS OF MATERIALS, AND APPARATUS FOR CARRYING OUT THE METHOD

The invention relates to a method for X-ray analysis of materials, comprising formation of an X-ray beam in a given region to be irradiated, irradiation of a specimen of the material to be analysed which is arranged in the region to be irradiated, detection of X-rays, excited in the specimen by the irradiating X-ray beam, by means of a detector which detects the spatially integrated value of the radiation, and the spatial selection of that part of the X-rays emanating from the specimen which exits at a grazing angle relative to the specimen surface.

The invention also relates to an apparatus for carrying out the method.

A method of the kind set forth is described in an article by T. Noma and A. Iida: "Surface analysis of layered thin films using a synchrotron x-ray microbeam combined with a grazing-exit condition", published in Rev. Sci. Instr. 65(4), Apr. 1994, pp. 837–844.

Generally speaking, for X-ray analysis of materials it is desirable to achieve an as high as possible signal-to-noise ratio in the beam emanating from the specimen. The signal is in that case the intensity of X-rays excited by the material under the influence of an X-ray beam incident on the specimen in the region of importance; in many applications this is notably the surface thereof (as for the study of the surfaces of integrated circuits). Noise is in that case caused by X-rays scattered in deeper layers of the specimen.

An analysis method is known in which a very attractive signal-to-noise ratio is achieved by utilizing grazing incidence of the X-rays. The noise component of the radiation emanating is thus strongly reduced. This technique is known as total-reflection X-ray fluorescence with grazing incidence (GI-XRF). According to this technique, after monochromatization and parallelization the X-rays are incident on a specimen in such a manner that the angle between the specimen surface and the incident parallel beam is smaller than the limit angle for total reflection of X-rays. The X-rays thus excited in the specimen are intercepted by an Si(Li) detector which is arranged at a very small distance from the irradiated region of the specimen.

Because according to the known method the incident beam is to enclose a very small angle (of the order of magnitude of between 0.01° and 1°) relative to the specimen surface, very severe requirements are imposed as regards parallelism of the incident beam. This means that only a small part of the radiation generated by the X-ray tube can be utilized, because X-rays can be parallelized only by removal of the non-parallel part from the beam, for example by way of a multilayer mirror. This means that the radiation emanating from the specimen also has a comparatively low intensity. In order to enable effective measurement despite this low intensity, use is made of a detector which intercepts the X-rays emanating from the specimen with a large solid angle, so that the amount of radiation lost to detection at the exit side is minimized. Therefore, use is made of a detector which has a large detection surface area and which is arranged near the specimen, for example said Si(Li) detector.

The cited article describes a related analysis method in which an attractive signal-to-noise ratio is also achieved, notably by taking off the excited X-rays at a very small angle relative to the specimen surface. The noise component in the emanating radiation is thus also strongly reduced. This technique is known as total-reflection X-ray fluorescence with grazing exit (XRF with Grazing Exit or GE-XRF).

In the case of grazing exit it is not necessary to parallelize the incident X-ray beam, so that the full intensity produced by the X-ray source can be used to irradiate the specimen. Moreover, it is no longer necessary to arrange a collimator between the X-ray source and the specimen, so that the X-ray source can be arranged at a much shorter distance from the specimen; the X-ray intensity for the specimen is thus further increased.

The GE-XR arrangement described in the cited article (notably with reference to FIG. 1 and the associated section II on pages 837 and 838) comprises an X-ray source in the form of a synchrotron whose X-rays are incident on a specimen after monochromatization. The X-rays thus excited in the specimen are intercepted by an Si(Li) detector.

Before the X-rays from the synchrotron reach the specimen, the X-ray beam is given a very small cross-section (6.7×5.7 µm) at the area of the specimen by means of focusing X-ray mirrors, said small cross-section enabling examination of small parts of the specimen surface. The focusing X-ray mirrors are fused quartz mirrors provided with a layer of platinum; their effect is based on the total X-ray reflection phenomenon for which the X-rays must be incident at a very small angle relative to the mirror surface.

The method described in the cited article is aimed at X-ray fluorescence with a high spatial resolution, both in directions parallel to the specimen surface and in directions perpendicular thereto. The perpendicular resolution is thus obtained by application of the GE-XRF technique and the parallel resolution by the use of a very small beam cross-section.

Because the X-rays are incident at a very small angle relative to the mirror surface of the focusing mirrors, only a very small pan of the solid angle of the X-ray source is used. This is not objectionable in the known arrangement because a synchrotron produces X-rays of an intensity which is substantially higher (by a factor of more than 1000) than a conventional X-ray source as used in commercially available X-ray analysis equipment. If a conventional X-ray tube were used as the X-ray source, the intensity would be so low that GE-XRF measurements would be impossible because of the strongly degraded signal-to-noise ratio. However, synchrontrons are very large and expensive apparatus which are available at a very limited scale only, that is to say in a few large research laboratories.

It is an object of the invention to provide a method of the kind set forth which enables GE-XRF measurements to be performed while utilizing an X-ray source in the form of a conventional X-ray tube.

To this end, the method of the invention is characterized in that the exciting X-ray beam forms an irradiation pattern of predetermined geometry at the area of the specimen, that the specimen and the irradiation pattern are displaced relative to one another during the measurement, and that the radiation detected during this measurement is subjected to an operation which determines from the spatially integrated value of the radiation the radiation originating from a locally limited region of the specimen, the shape of the pattern and the method of displacement being determined by the operation to be performed.

As a result of the use of said operation, the irradiation pattern at the area of the specimen need not have the very small dimensions of the locally limited specimen region to be analysed, but may be much larger. Generally speaking, an irradiation pattern of, for example a width of 0.1 mm and a length of some tens of mm could be used. Such an irradiation pattern can be readily formed by shielding a conventional X-ray tube by means of a slit mask. By moving the rectangular irradiation pattern thus formed across the specimen, or by displacing the specimen (having the same effect, the spatially integrated value (the mean value) of the radiation excited by the irradiating beam is each time measured by the detector. A suitable processing method which determines from the spatially integrated value of the radiation the radiation originating from a locally limited specimen region, then supplies the desired information which otherwise would have to be obtained by using an X-ray microbeam (i.e. the X-ray beam of very small cross-section).

A suitable processing method which satisfies the described requirements is known per se from an article in *Advances in X-ray Analysis*, Vol. 23, pp. 263–272:"X-ray imaging" by N. Gurker. A reconstruction technique which can be used for the described purpose is proposed notably with reference to FIG. 9 and the associated formules.

In conformity with a further step of the invention, the method is characterized in that the detector detecting the spatially integrated value of the radiation is constructed as a wavelength-dispersive detector.

In a detector of the wavelength-dispersive type, each photon is converted into an electric pulse whose pulse height and/or charge contents are not discriminated. Thus, in this detector exclusively the number of photons is determined. Such a detector is formed, for example by an assembly consisting of successively a collimator, an analysis crystal and an X-ray counter tube. The collimator selects the radiation of the desired direction from the beam emanating from the specimen, which radiation is subsequently incident on the analysis crystal. In accordance with the known Bragg law, this crystal reflects practically only one wavelength, i.e. the wavelength associated with the angle of incidence (and an immediate vicinity thereof, for example 0.05°) of the selected radiation. The entire desired range of angles of incidence can be covered, and hence also the associated range of wavelengths, by rotation of the analysis crystal during the measurement. The relationship between the radiation intensity (being proportional to the counting speed of the counter tube) and the wavelength is thus established. Because the radiation applied to the analysis crystal must be strictly parallel, this crystal is preceded by a collimator, for example a Sollet slit. One consequence of the parallelization of the radiation emanating from the specimen consists in that its intensity is reduced, but as a result of the steps taken in accordance with the GE-XRF measuring method, the intensity of the radiation excited by the specimen is so high that the loss incurred due to parallelization can be accepted so that a wavelength-dispersive detector can be used. The advantage of such a detector resides in the fact that, as opposed to an energy-dispersive detector, it is also capable of detecting soft X-rays originating from light elements. (Generally speaking, X-rays excited by elements whose atomic number is lower than 11 cannot be measured by means of an energy-dispersive detector; in this respect see also "*Principles and Practice of X-ray Spectrometric Analysis*" $2^{nd}$ ed. by Eugene P. Benin, Plenum Press, New York—London, chapter 6, paragraph 4).

In conformity with another step of the invention, the method is characterized in that the specimen of the material to be examined is irradiated by forming the appearance of the irradiating beam by means of a bundle of X-ray-optical fibres.

X-ray-optical fibres are known per se. They utilize total reflection of X-rays on the inner wall of the hollow fibre which can be provided with an appropriate layer for this purpose. This step enables simple adaptation of the shape of the irradiated part to the user's requirements by imparting the desired shape to the exit end of the fibre bundle. This can be realised with a loss of intensity which is much smaller than in known methods for influencing the appearance of an X-ray beam, for example shielding or use of X-ray mirrors, which are always accompanied by high X-ray losses.

In accordance with a further step of the invention, the method is characterized in that the bundle of fibres is constructed so that the cross-sectional area of the X-ray beam emanating from the bundle of X-ray-optical fibres is the same as that of the X-ray beam accepted by the bundle of fibres, and that the width of the emanating X-ray beam is less than 0.2 mm.

The X-ray beam thus formed has an appearance which, because of its simple shape and comparatively small width is readily compatible with said processing method in achieving a suitable resolution in combination with a simple construction of the fibre bundle.

The invention will be described with reference to the Figures of the drawing.

Figure 1:
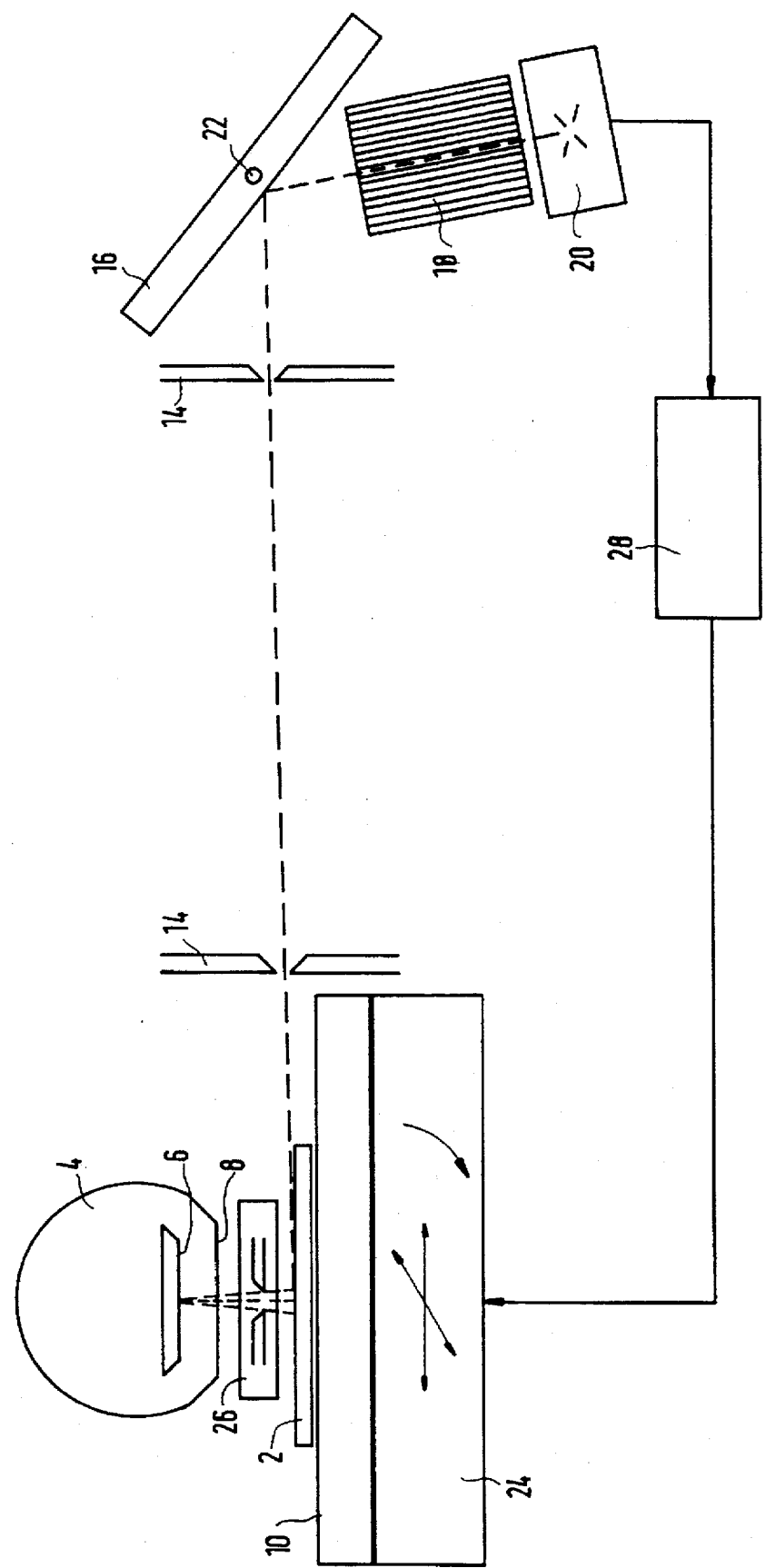
FIG. 1 shows diagrammatically the arrangement of the relevant elements of an apparatus for X-ray analysis in accordance with the invention.

As shown in FIG. 1a a specimen 2 is irradiated by X-rays from an X-ray source 4 in the form of a conventional X-ray tube. X-rays are generated in said tube by an X-ray anode 6, which rays leave the tube via a window 8. The wavelength spectrum of the tube can be chosen at option as a well-defined spectral line or as a wide spectrum. To this end, the window 8 is preferably constructed so as to have a shape which transmits a wide spectrum of X-rays with the least attenuation. If desired, for the selection of a wavelength range a known radiation filter (not shown in the Figure) may be arranged between the tube and the specimen. In the beam path between the X-ray tube and the specimen there is arranged an element 26 for limiting or shaping the exciting X-ray beam in such a manner that at the area of the specimen an irradiation pattern of desired geometry arises. This element may be shaped as a slit, so that the geometry of the irradiation pattern is shaped as an elongate rectangle. The element 26 may also be constructed as a bundle of X-ray fibres. One end face of this bundle may then face the anode, so that an as large as possible part of the X-rays emitted by the tube 28 is intercepted by the fibres of the bundle. The other end of the fibre bundle may then be oriented towards the specimen and have an appropriate shape, for example the already mentioned shape of an elongate rectangle.

With a view to achieving an optimum radiation intensity on the specimen, the X-ray tube 4 can be arranged at an arbitrarily short distance from the specimen, said distance being restricted only by the space occupied by the intermediate elements, such as said radiation filter or the beam shaping element 26. The specimen is arranged on a specimen support 10 which is rotatable, if desired, about an axis (not shown) extending perpendicularly to the plane of drawing. If necessary, the exit angle of the radiation excited in the specimen can be adjusted by rotation about this axis. The specimen support is arranged on a table 24 which is constructed so that it enables translation in two mutually perpendicular directions, parallel to the surface of the specimen, and rotation about an axis extending perpendicularly to the specimen. The displacement of the specimen by this table is controlled by an arithmetic and control unit 28 which controls the step size and the direction of the various displacements.

The exit angle of the X-rays excited by the specimen is codetermined by a collimator system 14 which is rotatable about an axis (not shown) between the collimator slits and, if desirable, it is slidable in the excited X-ray beam so that the collimator system can be oriented relative to the specimen as desired. Moreover, in order to find the correct position relative to the specimen, the collimator system can also be rotated about an axis extending perpendicularly to and through the slits, and about an axis extending perpendicularly to the latter axis and situated in the space between the slits.

Subsequent to the collimator system there is arranged an analysis crystal 16 which is known per se and which serves to analyse the radiation generated in the specimen according to wavelength. As is known, X-rays incident on a monocrystal are reflected only at very well-defined angles in conformity with the Bragg reflection condition which is known from X-ray diffraction, said angles also being dependent on the wavelength. The collimator system 14 defines an exact angle of incidence on the analyser crystal. By rotating the crystal about a shaft 22 extending parallel to the collimator slits, a range of angles of incidence is covered and hence a range of reflected wavelengths. The analyser crystal is manufactured in such a manner (i.e. as a so-called mosaic crystal, being a multitude of monocrystals which are all oriented in substantially the same way so that they behave practically as one monocrystal) that the reflection angle exhibits a spread of the order of magnitude of 0.05°, so that sufficient reflected intensity remains even in the case of a low incident intensity on the crystal.

Subsequent to the analyser crystal there is arranged a further collimator 18. The collimator 18 serves to minimize any radiation generated in the analyser crystal by crystal fluorescence and by dispersion. The collimator 18 may be constructed as a known Soller slit. The radiation emanating from the collimator 18 is incident on a detector 20, for example a gas-filled counter tube which is sensitive to soft X-rays as originating from elements in the specimen whose atomic number is lower than 11. The X-ray intensity measured by the detector is applied to an arithmetic and control unit 28 in a manner to be described hereinafter.

The assembly formed by the X-ray tube 4 and the specimen 2 and the entire path between the specimen and the detector can be accommodated in a vacuum envelope, so that absorption of notably the soft X-rays by ambient air is counteracted.

Figure 2:
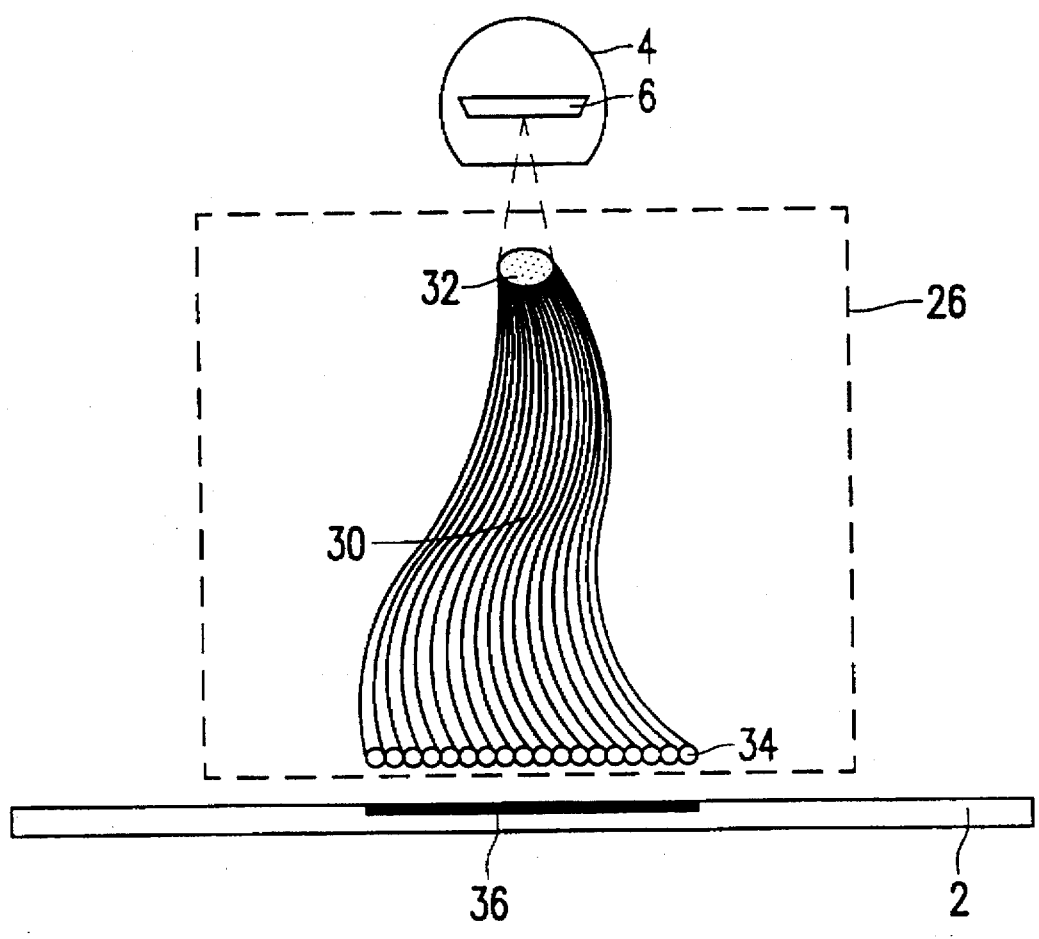
FIG. 2 shows diagrammatically a beam forming element of the apparatus of FIG. 1 employing a bundle of X-ray optical fibers.

During execution of the method of the invention, the specimen is irradiated with an irradiation pattern of predetermined geometry of the exciting X-ray beam, for example a geometry in the form of an elongate rectangle. The specimen is exposed a number of times in succession by means of said rectangle, each time a different pan of the specimen surface being exposed. The respective parts of the specimen to be exposed can be selected by displacement of the specimen by means of the table 24; however, it is alternatively possible to displace the beam shaping element 26 and to keep the specimen stationary. It is merely important that different pans of the specimen are successively exposed. Upon each exposure the intensity measured by the detector is read by the arithmetic and control unit 28 which stores, for each measurement, the associated position and the position of the exposure rectangle and the measured intensity in a memory. FIG. 2 shows an embodiment of the beam shaping element 26, arranged in the beam path between the X-ray tube 4 and the specimen 2, constructed as a bundle of X-ray fibers 30. One end of this bundle 30 faces the anode 6, in such a manner so that as large a possible part of the X-rays emitted by the tube is intercepted by the fibers of the bundle. The other end 34 of the fiber bundle is oriented towards the specimen 2 and has an appropriate shape, for example the already mentioned elongated rectangle. This rectangular shape provides a rectangular X-ray spot on the specimen 2.

During execution of the measurement, the specimen surface is subdivided into an imaginary matrix of pixels. When exposure takes place by means of a rectangular beam, during each exposure the detector measures the sum of the intensities of the individual pixels (the spatially integrated value of the radiation). Each measurement thus provides an equation consisting of the sum of the individual intensities which is equal to the total intensity measured during the relevant measurement. When the exposure rectangle is assumed to contain N pixels, therefore, at least N exposures must be carried out so as to obtain a set of equations that can be solved. The intensity originating from a given pixel can thus be determined. The method of solving a set of N equations with N unknowns is generally known and need not be explained herein.

For the processing of the measuring data originating from a locally limited region of the specimen (i.e. the pixel of interest) notably the cited processing method by N. Gurker can be chosen. The shape of the pattern and the method of displacement thereof across the specimen are determined by the operation to be carried out. Said processing methods opts for an irradiation pattern of an elongate rectangular shape. Said article gives an indication as regards the displacement of the irradiating beam. Further details relating to this method of signal processing can be derived from a contribution by A.M. Cormack "Radon's problem—old and new", to a book entitled Inverse Problems, Vol. 14, pp. 33–39 (Proceedings of the symposium in applied mathematics of the American Mathematical Society and the Society for Industrial and Applied Mathematics, Apr. 12–13, 1983).

I claim:

1. A method for X-ray analysis of materials, comprising:

formation of an X-ray beam in a given region to be irradiated, irradiation of a specimen (2) of the material to be analysed which is arranged in the region to be irradiated, detection of X-rays, excited in the specimen (2) by the irradiating X-ray beam, by means of a detector (16, 18, 20) which detects the spatially integrated value of the radiation, spatial selection of that pan of the X-rays emanating from the specimen which exits at a grazing angle relative to the specimen surface, characterized in that the exciting X-ray beam forms an irradiation pattern of predetermined geometry at the area of the specimen (2), the specimen (2) and the irradiation pattern are displaced relative to one another during the measurement, the radiation detected during this measurement is subjected to an operation which determines from the spatially integrated value of the radiation the radiation originating from a locally limited region of the specimen, the shape of the pattern and the method of displacement are determined by the processing operation to be performed.

2. A method as claimed in claim 1, characterized in that the detector (16, 18, 20) detecting the spatially integrated value of the radiation is constructed as a wavelength-dispersive detector.

3. A method as claimed in claim 1, characterized in that the specimen (2) of the material to be examined is irradiated by forming the appearance of the irradiating beam by means of a bundle of X-ray-optical fibres.

4. A method as claimed in claim 2, characterized in that the bundle of fibres is constructed so that the cross-sectional area of the X-ray beam emanating from the bundle of X-ray-optical fibres is the same as that of the X-ray beam accepted by the bundle of fibres, and that the width of the emanating X-ray beam is less than 0.2 mm.

5. An apparatus for X-ray analysis of materials, comprising:

an X-ray source (4, 6) for forming an X-ray beam in a given region to be irradiated, a specimen support (10) for supporting a specimen of the material to be examined which is arranged in the region to be irradiated, a detector (16, 18, 20) for detecting X-rays excited by the irradiating X-ray beam in the specimen, said detector detecting the spatially integrated value of the radiation, the apparatus comprising selection means for the spatial selection of that part of the X-rays emanating from the specimen which exists at a grazing angle relative to the specimen surface, said selected part of the radiation being applied to the detector, characterized in that the apparatus comprises means for forming an irradiation pattern of predetermined geometry at the area of the specimen (2) by means of the exciting X-ray beam, the specimen support (10) is rotatable as well as translatable in its own plane relative to the irradiation pattern, the apparatus comprises means for subjecting the radiation detected during the measurement to an operation which determines from the spatially integrated value of the radiation the radiation which originates from a, locally limited region of the specimen.

6. An apparatus as claimed in claim 5, characterized in that the detector (16, 18, 20) for the detection of the X-rays emanating from the specimen is constructed as a wavelength-dispersive detector.

7. An apparatus as claimed in claim 5, characterized in that a bundle of X-ray-optical fibres is arranged between the X-ray source (4, 6) and the specimen support (10).

8. An apparatus as claimed in claim 7, characterized in that the bundle of X-ray-optical fibres is constructed so that the cross-sectional area of the X-ray beam emanating from the bundle of X-ray-optical fibres is the same as that of the X-ray beam accepted by the bundle of fibres, and that the width of the emanating X-ray beam is less than 0.2 mm.

\* \* \* \* \*